(12) United States Patent
Watanabe

(10) Patent No.: US 10,962,453 B2
(45) Date of Patent: Mar. 30, 2021

(54) PATHOLOGICAL SPECIMEN, METHOD FOR PRODUCING PATHOLOGICAL SPECIMEN, AND METHOD FOR ACQUIRING FLUORESCENCE IMAGE

(71) Applicant: KONICA MINOLTA, INC., Chiyoda-ku (JP)

(72) Inventor: Yasuhiro Watanabe, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 15/736,171

(22) PCT Filed: Jun. 1, 2016

(86) PCT No.: PCT/JP2016/066197
§ 371 (c)(1),
(2) Date: Dec. 13, 2017

(87) PCT Pub. No.: WO2016/203952
PCT Pub. Date: Dec. 22, 2016

(65) Prior Publication Data
US 2018/0156699 A1 Jun. 7, 2018

(30) Foreign Application Priority Data
Jun. 16, 2015 (JP) .............................. JP2015-120955

(51) Int. Cl.
*G01N 1/30* (2006.01)
*G01N 33/533* (2006.01)
*G01N 21/64* (2006.01)
*G01N 33/53* (2006.01)
*G01N 1/28* (2006.01)
*G01N 33/48* (2006.01)
*G01N 33/58* (2006.01)

(52) U.S. Cl.
CPC ............... *G01N 1/30* (2013.01); *G01N 1/28* (2013.01); *G01N 21/64* (2013.01); *G01N 21/6428* (2013.01); *G01N 33/48* (2013.01); *G01N 33/53* (2013.01); *G01N 33/533* (2013.01); *G01N 33/587* (2013.01); *G01N 2001/302* (2013.01); *G01N 2021/6439* (2013.01); *G01N 2458/00* (2013.01)

(58) Field of Classification Search
CPC ....................................................... G01N 1/28
See application file for complete search history.

(56) References Cited

U.S. PATENT DOCUMENTS

2013/0157895 A1\* 6/2013 Aimiya .................. G01N 1/30
506/9

FOREIGN PATENT DOCUMENTS

| JP | 7-6747 | 1/1995 |
|---|---|---|
| JP | H07-35357 | 2/1995 |
| JP | 2012-205572 | 10/2012 |
| JP | 2012-532846 | 12/2012 |
| JP | 2015-59806 | 3/2015 |
| WO | WO 2013/035703 | 3/2013 |
| WO | WO 2013/147081 | 10/2013 |
| WO | WO 2014/136776 | 9/2014 |

OTHER PUBLICATIONS

Blythe et al., J Clin Pathol., 1997, 50:45-49.*
Gerrits et al., The J of Histotechnology, 1996, 19(4):297-311.*
Zhang et al., J Mol Diagn., 2013, 15:754-764.*
Cytoseal60 data sheet, 1 page.*
Search Report and a Written Opinion dated Aug. 16, 2016 which issued in the corresponding International Patent Application No. PCT/JP2016/066197.
Office Action dated Dec. 17, 2019 issued in Japanese Patent Application No. 2018-233580.

\* cited by examiner

*Primary Examiner* — Bin Shen
(74) *Attorney, Agent, or Firm* — Cozen O'Connor

(57) ABSTRACT

A signal of fluorescence emitted from a fluorescent particle of a pathological specimen can be increased in sensitivity and be stabilized, thereby resulting in an enhancement in retrieval accuracy of information from a fluorescence image. A pathological specimen including a tissue section subjected to a treatment (immunostaining/FISH staining treatment) for fluorescence-labeling of an objective biomaterial with a fluorescent particle observable in a dark field, based on an immunostaining or FISH method; a packed layer with which the tissue section is covered; and a protection layer with which the packed layer is covered; wherein
the refractive indexes of the fluorescent particle, the packed layer and the protection layer (measurement wavelength: 589 nm; measurement temperature: 20° C.; in all) satisfy the conditions of Expressions (1) and (2):

$$|n1-n2| \leq 0.20 \quad \text{Expression (1)}$$

$$|n2-n3| \leq 0.15 \quad \text{Expression (2)}$$

n1: refractive index (fluorescent particle)
n2: refractive index (packed layer)
n3: refractive index (protection layer).

17 Claims, 2 Drawing Sheets

[Fig. 1]
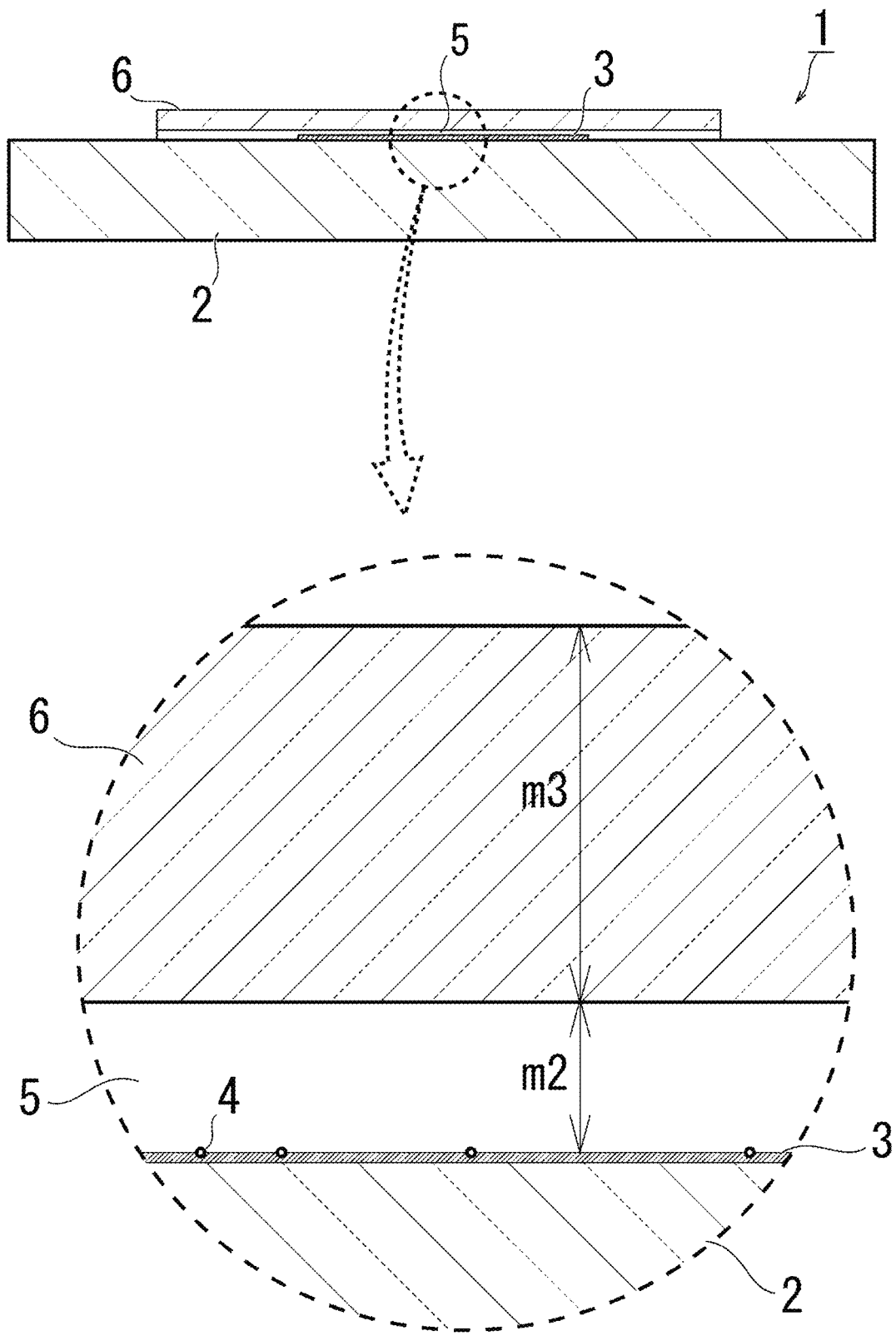

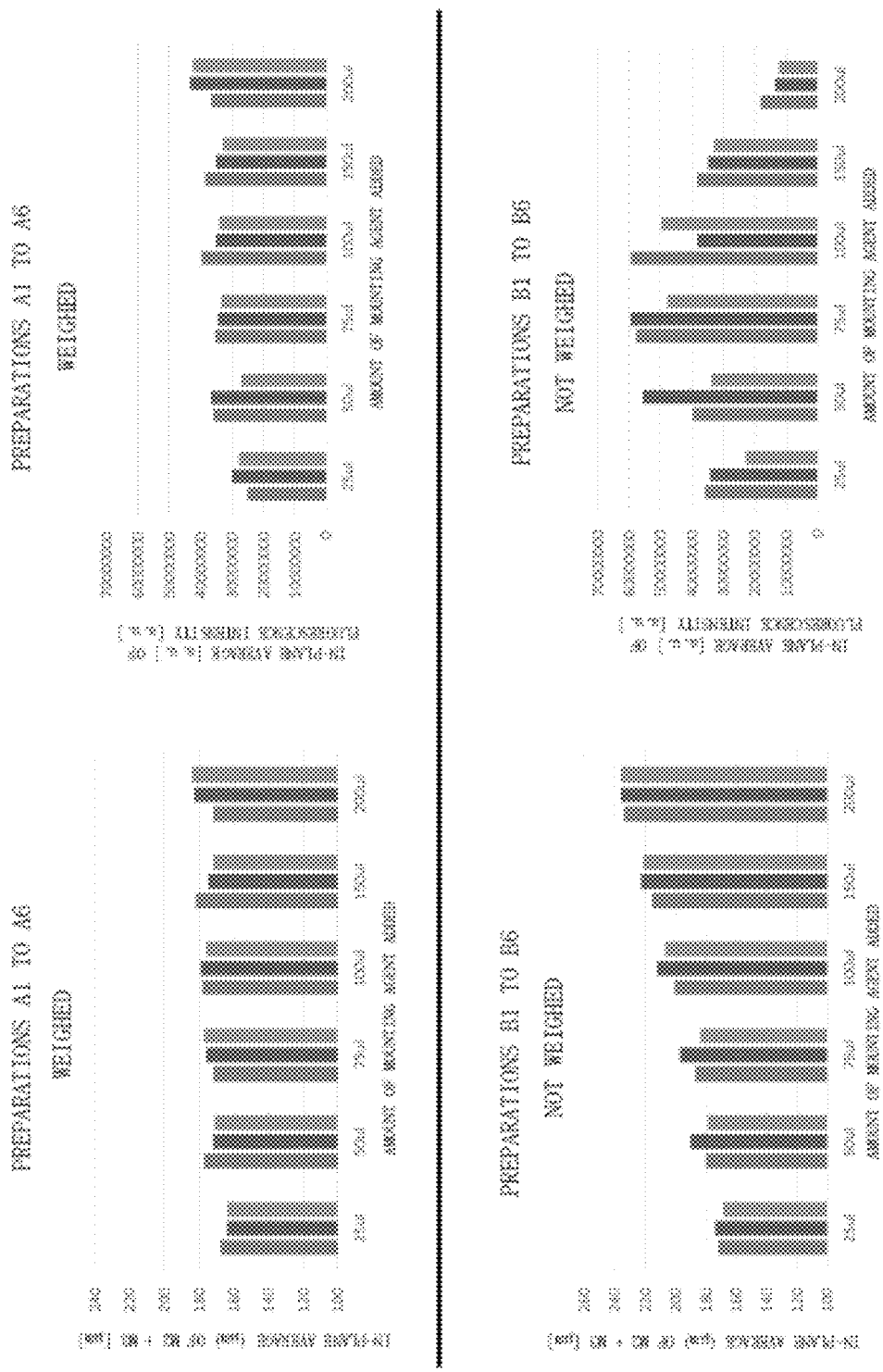
[Fig. 2]

PATHOLOGICAL SPECIMEN, METHOD FOR PRODUCING PATHOLOGICAL SPECIMEN, AND METHOD FOR ACQUIRING FLUORESCENCE IMAGE

RELATED APPLICATIONS

This is a U.S. National Phase Application under 35 USC 371 of International Application PCT/JP2016/066197 filed on Jun. 1, 2016.

This application claims the priority of Japanese application no. 2015-120955 filed Jun. 16, 2015, the entire content of which is hereby incorporated by reference.

TECHNOLOGICAL FIELD

The present invention relates to a method in which an image (fluorescence image, dark field image) representing expression of an objective biomaterial produced from a pathological specimen by a fluorescent spot is used and the image is typically superimposed with an image (cellular morphology image, bright field image) representing the morphology of a cell produced from the same pathological specimen, thereby determining the position and amount of the objective biomaterial expressed in each cell area of the pathological specimen.

BACKGROUND

In a pathological diagnosis, there are performed a series of processes of: preparing a slide on which a tissue section collected from a patient is sliced and placed; subjecting the slide to staining by a predetermined method, thereby producing a pathological specimen; thereafter taking a stained image of the pathological specimen; and acquiring information for a pathological diagnosis from the resulting stained image. The stained image acquired from the pathological specimen can be used to not only observe the morphology of a cell or tissue, but also quantify and evaluate the expression level of a specified biomolecule, thereby diagnosing various events, for example, whether the patient suffers from a specified disease or not, or whether a specified therapeutic drug is successful or not.

As one pathological diagnosis example, a pathological diagnosis is widely conducted in which a tissue section produced by collection of a cancer tissue is used to quantify and evaluate a HER2 gene (HER2/neu, c-erbB-2) being one cancer gene, and/or a HER2 protein which is a membrane protein produced from the HER2 gene and which is presumed to serve as a receptor of a cancer cell growth factor, thereby diagnosing prognosis for a breast cancer patient, or predicting the therapeutic effect of a molecular targeted therapeutic drug "trastuzumab" (trade name "Herceptin" (registered trademark), anti-HER2 monoclonal antibody). While amplification of the HER2 gene and overexpression of the HER2 protein are observed in 15 to 25% of human breast cancer cases, overexpression of HER2 in a cancer cell basically occurs according to gene amplification at the DNA level. A HER2 examination method directed to a cancer tissue is classified to a method of observing amplification at the DNA level, a method of observing overexpression at the RNA level, and a method of observing overexpression at the protein level. Representative examples of the respective examination methods at the protein level and at the DNA level include an immunostaining method or an immunohistochemistry (IHC) method, and a fluorescence in situ hybridization (FISH) method. Such HER2 examinations are of clinical importance, and respective standard procedures and criteria (score) of HER2 examinations according to the immunostaining method (IHC method) and the FISH method are defined by the 2007 ASCO/CAP guidelines.

The immunostaining method or the immunohistochemistry (IHC) method is a method of detecting the amount of a HER2 protein expressed on a cell membrane by use of a fluorescently labeled anti-HER2 antibody, on a formalin-fixed paraffin-embedded tissue section. While a conventional immunostaining method (original IHC method) adopted has been a method (enzyme antibody method, for example, DAB method) of utilizing an anti-HER2 antibody labeled with an enzyme which generates a dye in the addition of a predetermined substrate, an immunostaining method (fluorescence antibody method) has also been increasingly utilized which utilizes an anti-HER2 antibody labeled with a fluorescent body more excellent in distinguishability. In such an immunostaining method, in general, a slide (specimen) on which a formalin-fixed paraffin-embedded tissue section sliced is placed is prepared, and subjected to a deparaffinization treatment or the like and thus made suitable for immunostaining, and thereafter a fluorescently labeled antibody is reacted and thus bound to a HER2 protein on a cell membrane. The tissue section thus immunostained is, if necessary, subjected to a mounting treatment with a mounting agent containing a fading inhibitor, a cover glass is further placed thereon, and thereafter a fluorescence image is taken in a dark field under irradiation with predetermined excitation light. There are superimposed a fluorescence image (dark field image) where a fluorescent body with which the HER2 protein is labeled is expressed as a bright spot, and a cellular morphology image (bright field image) taken in a bright field for reference, where the cell membrane is stained with a staining agent, and thus the number of bright spots observed in a cell membrane area per cell is counted and whether the HER2 protein is abnormally expressed or not is discriminated based on the resulting value.

Embodiments of the immunostaining method (fluorescence antibody method), in particular, a method of using a fluorescent body-integrated nanoparticle as a fluorescent body, can be seen in, for example, Patent Document 1 (International Publication No. WO 2013/035703), Patent Document 2 (International Publication No. WO 2013/147081) and Patent Document 3 (International Publication No. WO 2014/136776).

RELATED ART DOCUMENTS

Patent Documents

Patent Document 1: International Publication No. WO 2013/035703
Patent Document 2: International Publication No. WO 2013/147081
Patent Document 3: International Publication No. WO 2014/136776

SUMMARY

Technical Problem

The fluorescence image described above is processed so that information usable in a pathological diagnosis is extracted. For example, processing is made which includes forming an image in which a bright spot area is extracted from the "fluorescence image", creating a "brightness profile" with respect to each bright spot area, and forming a "fluorescent particle image" in which a fluorescent particle in the bright spot area is extracted based on a "fluorescence profile" (reference profile) of one fluorescent particle serving as a fluorescent spot source. That is, the reference profile can be compared, with respect to each bright spot area, with the brightness profile of the bright spot area, thereby calculating the number of fluorescent particles and the position of each fluorescent particle in the bright spot area. The reference profile here can be created by imaging a single fluorescent particle in the same image-taking conditions as those of the fluorescence image of a pathological specimen. The number of fluorescent particles in each bright spot area included in one cell (cell membrane of one cell) can be counted and summed up, thereby determining the number of fluorescent particles per cell, namely, the number of molecules of an objective biomaterial (for example, HER2 protein) expressed in one cell. Furthermore, the number of fluorescent particles per cell with respect to each cell included in one fluorescence image can be determined and, if necessary, those in a plurality of fluorescence images can also be determined, thereby allowing information on the amount of the objective biomaterial expressed, for a pathological diagnosis, to be acquired.

When such image processing is performed, it is demanded to enhance the retrieval accuracy of information from the fluorescence image in order to create the brightness profile and the reference profile, and it is demanded for this to, for example, achieve "increase in sensitivity" so that fluorescence emitted from a fluorescent particle, even if being weak, can be certainly converted to a signal, and/or achieve "stabilization" so that fluorescence having a given intensity is converted to a signal having a given strength. There have been conventionally the problems of discrimination of a protein small in amount of expression, the in-plane variation in a pathological specimen (tissue section), the variation between pathological specimens, and the like, in acquisition and processing of a fluorescence image, and thus there has been room for improvement of increase in sensitivity and stabilization.

An object of the present invention is to provide a device which can increase the sensitivity of a signal of fluorescence emitted from a fluorescent particle of a pathological specimen and stabilize the signal, thereby resulting in an enhancement in retrieval accuracy of information from a fluorescence image.

Solution to Problem

The present inventors have found that, in general, in a case where a pathological specimen including a tissue section immunostained with a fluorescent particle, a packed layer (layer formed by a mounting agent) with which the tissue section is covered, and a protection layer (cover glass) with which the packed layer is covered has a relationship where the refractive index of the fluorescent particle and the refractive index of the packed layer satisfy a specified expression and a relationship where the refractive index of the packed layer and the refractive index of the protection layer satisfy a specified expression, the signal of fluorescence emitted from the fluorescent particle can be increased in sensitivity and stabilized as compared with a case where such expressions are not satisfied. In particular, the present inventors have focused on the refractive index of the fluorescent particle and have surprisingly found that the refractive index of the fluorescent particle satisfies a specified relationship with the refractive index of the packed layer, thereby contributing to increase in sensitivity and stabilization of a fluorescence signal. The present invention has been made based on such findings.

That is, one aspect of the present invention provides a pathological specimen having the following technical features:

A pathological specimen including a tissue section subjected to a treatment (immunostaining/FISH staining treatment) for fluorescence-labeling of an objective biomaterial with a fluorescent particle observable in a dark field, based on an immunostaining method or a FISH method; a packed layer with which the tissue section is covered; and a protection layer with which the packed layer is covered; wherein the refractive indexes of the fluorescent particle, the packed layer and the protection layer (measurement wavelength=589 nm and measurement temperature=20° C. in all) satisfy the conditions of the following Expressions (1) and (2):

$|n1-n2|\leq 0.20$      Expression (1)

$|n2-n3|\leq 0.15$      Expression (2)

n1: the refractive index of the fluorescent particle
n2: the refractive index of the packed layer
n3: the refractive index of the protection layer.

Another aspect of the present invention provides a method for producing a pathological specimen, having the following technical features:

A method for producing a pathological specimen, including: performing a treatment (immunostaining/FISH staining treatment) for fluorescence-labeling of an objective biomaterial with a fluorescent particle observable in a dark field, based on an immunostaining method or a FISH method; performing a treatment (packing treatment) for covering of the tissue section with a packed layer; and performing a treatment (protection treatment) for covering of the packed layer with a protection layer; wherein the refractive indexes of the fluorescent particle, the packed layer and the protection layer (measurement wavelength=589 nm and measurement temperature=20° C. in all) in the immunostaining/FISH staining treatment, the packing treatment and the protection treatment satisfy the conditions of the following Expressions (1) and (2):

$|n1-n2|\leq 0.20$      Expression (1)

$|n2-n3|\leq 0.15$      Expression (2)

n1: the refractive index of the fluorescent particle
n2: the refractive index of the packed layer
n3: the refractive index of the protection layer.

Still another aspect of the present invention provides a method for acquiring a fluorescence image, having the following technical features:

A method for acquiring a fluorescence image of the pathological specimen of the present invention, or a pathological specimen obtained by the production method of the present invention, including:

measuring the thickness (m2) of the packed layer and the thickness (m3) of the protection layer in the pathological specimen, thereby calculating the in-plane average (M (m2+m3)) of the sum of m2 and m3; and correcting the spherical aberration of a bright spot image of the fluorescent particle based on the in-plane average.

Advantageous Effects of Invention

The present invention can allow a signal of fluorescence emitted from a fluorescent particle of a pathological specimen to be stably acquired at a high sensitivity, allow the variation between a plurality of points in the same plane and the variation between samples to be suppressed, and allow the retrieval accuracy of information from a fluorescence image to be enhanced. Thus, it is possible to extract information higher in reliability, on the position and amount of expression of a specified gene, from the fluorescence image, and utilize the information in a pathological diagnosis.

BRIEF DESCRIPTION OF THE DRAWINGS

FIG. 1 schematically illustrates a pathological specimen including a tissue section immunostained with a fluorescent particle, a packed layer and a protection layer, and a partial enlargement of the pathological specimen.

FIG. 2 illustrates a graph representing the in-plane average (left portion) of the sum (m2+m3) of the thickness of a packed layer and the thickness of a protection layer and the in-plane average (right portion) of the fluorescence intensity, of each of preparations A1 to A6 (cover glass weighted) and preparations B1 to B6 (cover glass unweighted) produced in Examples. Three samples with respect to the same type of preparation (amount of mounting agent added) are subjected to measurement.

DETAILED DESCRIPTION OF EMBODIMENTS

In the description herein, the description according to the "pathological specimen" and the description according to the "method for producing a pathological specimen" can be mutually referenced and again applied to common matters between the technical matters according to the "pathological specimen" and the technical matters according to the "method for producing a pathological specimen", unless particularly noted. The refractive indexes herein are each a value obtained by measurement in standard measurement conditions of a measurement wavelength of 589 nm and a measurement temperature of 20° C., unless particularly noted.

—Pathological Specimen—

The pathological specimen of the present invention includes a tissue section subjected to a treatment (immunostaining treatment) for fluorescence-labeling of an objective biomaterial with a fluorescent particle observable in a dark field, based on an immunostaining method or a FISH method; a packed layer with which the tissue section is covered; and a protection layer with which the packed layer is covered; wherein the refractive indexes of the fluorescent particle, the packed layer and the protection layer (measurement wavelength=589 nm and measurement temperature=20° C. in all) satisfy the conditions of the following Expressions (1) and (2):

$$|n1-n2|\leq 0.20 \qquad \text{Expression (1)}$$

$$|n2-n3|\leq 0.15 \qquad \text{Expression (2)}$$

n1: the refractive index of the fluorescent particle
n2: the refractive index of the packed layer
n3: the refractive index of the protection layer.

In one embodiment of the present invention, furthermore, the thicknesses of the packed layer and the protection layer in the pathological specimen of the present invention preferably satisfy the condition of the following Expression (3):

$$CV(m2+m3)\leq 20\% \qquad \text{Expression (3)}$$

m2: the thickness of the packed layer
m3: the thickness of the protection layer

CV (m2+m3): the in-plane variation coefficient of the sum of m2 and m3.

Herein, the following is satisfied: variation coefficient=standard deviation/average.

In one embodiment of the present invention, furthermore, the thicknesses of the packed layer and the protection layer in the pathological specimen of the present invention preferably satisfy the conditions of the following Expressions (4) and (5):

$$10\ \mu m \leq M(m2) \leq 50\ \mu m \qquad \text{Expression (4)}$$

$$100\ \mu m \leq M(m3) \leq 200\ \mu m \qquad \text{Expression (5)}$$

m2: the thickness of the packed layer
m3: the thickness of the protection layer
M (m2): the in-plane average of m2
M (m3): the in-plane average of m3.

Not only the conditions according to Expressions (1) and (2), but also the condition according to Expression (3) and/or the conditions according to Expressions (4) and (5) can be satisfied, thereby allowing a signal of fluorescence emitted from a fluorescent particle of a pathological specimen to be increased in sensitivity and stabilized, to result in a further enhancement in the effect of enhancing the retrieval accuracy of information from a fluorescence image. The "in-plane average" of m2 and m3 means the average calculated from m2 and m3 measured at a plurality of points on one tissue section (area where the packed layer and the protection layer are provided), and the "in-plane variation coefficient" of the sum of m2 and m3 means the variation coefficient calculated from the sum of m2 and m3 measured at such a plurality of points. The number of in-plane measurement points is not particularly limited, and several points (4 to 6 points) to several tens points, for example, 10 to 20 points may be generally selected from the entire in-plane area.

(Tissue Section)

The tissue section forming the pathological specimen is collected from a subject (human or an animal such as another mammal) suffering from or suspected to suffer from a disease to be subjected to a pathological diagnosis, according to an ordinary method, and is subjected to predetermined pre-treatment, staining treatment and post-treatment.

The tissue section is usually used with being prepared so as to have a thickness of several μm and a size of 1 mm in square to several mm in square. Such a tissue section preferably has an in-plane average thickness falling within a given range in order that the brightness of a fluorescent particle is uniform as much as possible in acquisition of a fluorescence image. That is, in one embodiment of the present invention, the thickness of the tissue section preferably satisfies the condition of the following Expression (6):

$$2\ \mu m \leq M(m1) \leq 6\ \mu m \qquad \text{Expression (6)}$$

m1: the thickness of the tissue section
M (m1): the in-plane average of m1.

The tissue section is typically subjected to not only the treatment (immunostaining/FISH staining treatment) for fluorescence-labeling of an objective biomaterial with a fluorescent particle observable in a dark field, but also a treatment (bright-field staining treatment) for staining of a cell with a staining agent observable in a bright field. The position and amount of an objective biomaterial expressed in one cell can be accurately determined and evaluated by acquiring an image of immunostaining (fluorescence image) and an image of bright-field staining (cellular morphology image) in the same field by use of not a plurality of adjacent tissue sections (a plurality of pathological specimens where such tissue sections are placed one by one), but one tissue section, and performing predetermined image processing.

When immunostaining where a specified protein expressed in a cell is adopted as the objective biomaterial is performed, representative examples of a staining reagent for bright-field staining performed in combination therewith include hematoxylin for staining of a substance negatively charged, such as a cell nucleus, a calcified portion, a cartilage tissue, a bacteria, and mucus, to indigo blue to light blue, and/or eosin for staining of a substance positively charged, such as cytoplasm, a cell membrane, interstitium, various fibra, an erythrocyte, and a keratinocyte, to red to deep red. In particular, when a protein (membrane protein) expressed in a cell membrane is adopted as the objective biomaterial, eosin for staining of a cell membrane is preferably used (staining with eosin), and hematoxylin may also be simultaneously used (staining with hematoxylin/eosin: HE staining). Each of hematoxylin and eosin is prepared as an aqueous solution.

On the other hand, when FISH staining where a specified gene (nucleic acid having a specified base sequence) included in a nuclear chromosome is adopted as the objective biomaterial is performed, representative examples of a staining reagent for bright-field staining performed in combination therewith include DAPI (4,6-diamidino-2-phenylindole dihydrochloride) being a fluorescent dye intercalated into double-stranded DNA, and other nuclear staining agents. A nuclear staining reagent such as DAPI is also generally prepared as an aqueous solution.

(Fluorescent Particle)

The fluorescent particle is a particulate fluorescent body which is observable as a bright spot when irradiated with predetermined excitation light in a dark field. The average particle size of the fluorescent particle is usually 10 to 500 nm, preferably 50 to 200 nm, and the variation coefficient of the particle size is usually 20% or less, preferably 5 to 15%. The particle size of the fluorescent particle can be measured by taking an electron microscope photograph with a scanning electron microscope (SEM), measuring the cross-section area of a resin particle for fluorescence-labeling, and defining the cross-section area measured, as the area of the corresponding circle, to thereby determine the diameter of the circle (equivalent diameter of area circle). The average particle size is calculated as the arithmetic average of the respective particle sizes measured of a sufficient number (for example, 1000) of fluorescent particles included in a fluorescent particle population, and the variation coefficient is calculated according to Expression: 100×particle size standard deviation/average particle size.

The fluorescent particle is not particularly limited as long as the refractive index (n1) satisfies the condition of Expression (1), and can be appropriately selected in consideration of the refractive index (n2) of the packed layer.

For example, a fluorescent body-integrated nanoparticle can be used as the fluorescent particle. The fluorescent body-integrated nanoparticle is a nano-sized (1 µm or less in diameter) particulate fluorescent body obtained by encapsulation or attachment of a plurality of fluorescent bodies such as fluorescent dyes or semiconductor nanoparticles (quantum dots) into a substance serving as a base material or onto the surface thereof for integration. Use of such a fluorescent body-integrated nanoparticle for immunostaining is preferable as compared with use of a single fluorescent body (for example, one fluorescent dye molecule or one semiconductor nanoparticle) in that the intensity of fluorescence emitted from one fluorescent marker with which an objective protein is labelled can be increased, resulting in an enhancement in distinguishability from any noise such as autofluorescence of a cell and from other (fluorescent) dyes, and also resulting in suppression of discoloration due to irradiation with excitation light. The fluorescent body-integrated nanoparticle may also be, if necessary, modified by a hydrophilic compound such as a hydrophilic polymer from the viewpoint of suppression of non-specific adsorption by a hydrophobic bond.

A substance which can integrate a fluorescent body by means of a physical or chemical bonding force, such as a resin or silica, can be used as the base material forming the fluorescent body-integrated nanoparticle. When the fluorescent body-integrated nanoparticle is used as the fluorescent particle, the refractive index of the substance for use as the base material of the fluorescent body-integrated nanoparticle, such as a resin or silica, is assumed to be the refractive index n1 of the fluorescent particle.

Examples of the resin for producing the fluorescent body-integrated nanoparticle include thermosetting resins such as a melamine resin, a urea resin, a benzoguanamine resin, a phenol resin and a xylene resin; and various homopolymers and copolymers produced by use of at least one monomer, such as a styrene resin, an acrylic resin, polyacrylonitrile, an AS resin (acrylonitrile-styrene copolymer) and an ASA resin (acrylonitrile-styrene-methyl acrylate copolymer). Some resins and the refractive indexes thereof are exemplified as follows:

Melamine resin, refractive index: 1.48

Acrylic resin (polymethyl methacrylate), refractive index: 1.49

Styrene resin (polystyrene), refractive index: 1.59.

In one embodiment of the present invention, the fluorescent particle is preferably a fluorescent body-integrated nanoparticle including a resin as a base material, for example, a fluorescent body-integrated nanoparticle including a melamine resin, an acrylic resin or the like as a base material. Such a fluorescent particle has a refractive index n1 easily satisfying Expression (1), when a mounting agent containing an acrylic resin is used in the packed layer, for example. A melamine resin is here preferable from the viewpoints of allowing a nanoparticle with a fluorescent body such as a fluorescent dye integrated, to be easily produced, thereby providing a nanoparticle high in emission intensity, and of having hydrophilicity, thereby allowing non-specific adsorption to be easily prevented.

On the other hand, a substance which can emit fluorescence in the form of one molecule or one particle, such as a fluorescent dye or a semiconductor nanoparticle, can be used as the fluorescent body forming the fluorescent body-integrated nanoparticle. Any fluorescent body may be selected which emits fluorescence (color) at a desired wavelength in a stained image taken. When there are a plurality of objective biomolecules (for example, protein and/or nucleic acid) to be fluorescently labeled, a plurality of fluorescent bodies which correspondingly emit fluorescence at respective different wavelengths may be used in combination.

Examples of the fluorescent dye include a fluorescein-based dye, a rhodamine-based dye, an Alexa Fluor (registered trademark, produced by Invitrogen)-based dye, a BODIPY (registered trademark, produced by Invitrogen)-based dye, a Cascade (registered trademark, Invitrogen)-based dye, a coumarin-based dye, an NBD (registered trademark)-based dye, a pyrene-based dye, a cyanine-based (Cy-based) dye, a perylene-based dye, an oxazine-based dye, and a fluorescent dye made of a low-molecular organic compound (which is not a polymeric organic compound such as a polymer).

Specific examples can include 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2',7'-dimethoxyfluorescein and naphthofluorescein (all are fluorescein-based dyes); 5-carboxy-rhodamine, 6-carboxy-rhodamine, 5,6-dicarboxy-rhodamine, rhodamine 6G, tetramethylrhodamine, X-rhodamine, sulforhodamine 101 and sulforhodamine 101 acid chloride (Texas Red (registered trademark)) (all are rhodamine-based dyes); Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700 and Alexa Fluor 750 (all are Alexa Fluor-based dyes); BODIPY FL, BODIPY TMR, BODIPY 493/503, BODIPY 530/550, BODIPY 558/568, BODIPY 564/570, BODIPY 576/589, BODIPY 581/591, BODIPY 630/650 and BODIPY 650/665 (all are BODIPY-based dyes); methoxycoumarin (coumarin-based dye); eosin, NBD (NBD-based dye); pyrene (pyrene-based dye); perylene diimide (perylene-based dye); and Cy5, Cy5.5 and Cy7 (Cy-based dyes). Any of such fluorescent dyes may be used singly, or a plurality of such fluorescent dyes may be used in combination.

Among them, rhodamine-based dyes such as Texas Red (registered trademark) corresponding to sulforhodamine 101 and hydrochloride thereof, and perylene-based dyes such as perylene diamide and derivatives thereof are preferable because of being relatively high in light resistance.

In one embodiment of the present invention, the emission wavelength of the fluorescent particle (a fluorescent dye or a semiconductor nanoparticle contained in the fluorescent body-integrated nanoparticle) preferably satisfies the condition of the following Expression (7):

$$550 \text{ nm} \leq \lambda 1 \leq 650 \text{ nm} \qquad \text{Expression (7)}$$

$\lambda 1$: the local maximum emission wavelength of the fluorescent particle

The fluorescent dye satisfying the condition of Expression (7) emits fluorescence appearing in yellow to red due to irradiation with predetermined excitation light, and can be appropriately selected from known fluorescent dyes by those skilled in the art.

On the other hand, the semiconductor nanoparticle (quantum dot) preferably emits visible to near-infrared light at a wavelength ranging from 400 to 1100 nm when excited by ultraviolet to near-infrared light at a wavelength ranging from 200 to 700 nm. Examples of such a semiconductor nanoparticle include a Group II-VI compound, a Group III-V compound, or a particle of a Group IV element (CdSe, CdS, CdTe, ZnSe, ZnS, ZnTe, InP, InN, InAs, InGaP, GaP, GaAs, Si, Ge or the like), or a core/shell type particle (CdSe/ZnS, CdS/ZnS, InP/ZnS, InGaP/ZnS, Si/SiO$_2$, Si/ZnS, Ge/GeO$_2$, Ge/ZnS or the like) where such a particle as a core is surrounded by a compound serving as a shell. Any of such semiconductor nanoparticles may be used singly, or a plurality of such semiconductor nanoparticles may be used in combination.

The above fluorescent body-integrated nanoparticle is a known substance, and the details of the fluorescent body and the base material for use in production thereof, and the production method thereof, as well as specific examples of embodiments thereof can be seen in, for example, International Publication No. WO 2013/035703, International Publication No. WO 2013/147081, and International Publication No. WO 2014/136776.

A fluorescent body-integrated nanoparticle including silica as a base material, other than the fluorescent body-integrated nanoparticle including a resin as a base material, can also be used as the fluorescent particle. The refractive index of silica is 1.44 to 1.50, and therefore silica can be used as the base material, thereby producing a fluorescent particle (fluorescent body-integrated nanoparticle) having a refractive index n1 ranging from 1.44 to 1.50.

While the semiconductor nanoparticle (quantum dot) by itself can also be here one type of the fluorescent particle, it generally has a higher refractive index than a resin and silica. For example, the refractive index of InP is 3.5 and the refractive index of GaAs is 3.8. Accordingly, for example, when a mounting agent having a refractive index n2 of around 1.50, as described below, is used to form the packed layer, use of the semiconductor nanoparticle as the fluorescent particle cannot allow the condition of Expression (1) to be satisfied. As long as there is any packed layer which can satisfy the condition of Expression (1), however, an embodiment where the semiconductor nanoparticle is used as the fluorescent particle is not excluded from the present invention.

(Packed Layer)

The packed layer is a layer with which the tissue section subjected to an immunostaining/FISH staining treatment is covered, in other words, a layer packed between the tissue section and the protection layer, and is typically a layer formed from a mounting agent.

The thickness m2 of the packed layer can be then determined by, for example, measuring the gap between the protection layer and the slide glass, and subtracting the thickness of the tissue section from the gap.

The packed layer, namely, the mounting agent for forming the packed layer is not particularly limited as long as the refractive index (n2) satisfies the conditions of Expressions (1) and (2), and can be appropriately selected in consideration of the refractive index (n1) of the fluorescent particle and the refractive index (n3) of the protection layer. The mounting agent encompasses a mounting agent to be solidified and a mounting agent not to be solidified. Although a mounting agent to be solidified may be varied in refractive index before and after solidification, the refractive index thereof is a value in the form of the finished pathological specimen, namely, is usually defined as the refractive index n2 obtained after solidification of the mounting agent to be solidified. The mounting agent can be roughly classified to a lipid-soluble (oil-based, water-insoluble) mounting agent and a water-soluble (aqueous) mounting agent, and any of them may be used.

The mounting agent is generally a mixture of a resin with a solvent for dissolution and dilution of the resin, and may be a commercial product or may be self-prepared. When the mounting agent is self-prepared, it may be prepared by mixing an appropriate synthetic resin or natural resin with an appropriate aqueous solvent or oily solvent (organic solvent) according to an ordinary method. A commercially available lipid-soluble mounting agent, if necessary, whose viscosity is adjusted by addition of an organic solvent, may also be used.

Examples of the commercially available lipid-soluble mounting agent product include the following products:

"Entellan (registered trademark) new", Merck KGaA, refractive index: 1.49 to 1.51, main component: acrylic resin, solvent: xylene (about 60%)

"PARAmount (registered trademark) N", FALMA, refractive index: 1.51, main component: acrylic resin, solvent: aliphatic hydrocarbon (non-xylene, non-toluene)

"MOUNT QUICK", Daido Sangyo Co., Ltd., refractive index: 1.41, main component: acrylic resin-"ProLong (registered trademark)", Life Technologies Japan Ltd. (Thermo Fisher Scientific), refractive index: 1.46, main component: acrylic resin "Malinol", MUTO PURE CHEMICALS CO. LTD., refractive index: 1.57, main component: acrylic resin.

Examples of the commercially available water-soluble mounting agent include the following products:

"VECTASHIELD (registered trademark)", Vector Laboratories, refractive index: 1.36, main component: glycerin.

The refractive index of the packed layer formed from the mounting agent is generally affected by both of the refractive index of the resin included in the mounting agent and the refractive index of the solvent. When a mounting agent to be solidified is used, the solvent is gradually evaporated as the mounting agent is dried and solidified, and therefore the refractive index of the packed layer mainly corresponds to a value reflecting the refractive index of the remaining resin. On the other hand, when a mounting agent not to be solidified is used, the solvent is also present in a certain amount and therefore the refractive index of the packed layer corresponds to a value reflecting the refractive indexes of both the resin and the solvent (the value falls within the range from the upper limit being one of such refractive indexes to the lower limit being the other thereof).

Examples of the organic solvent compounded to the lipid-soluble mounting agent include an aromatic hydrocarbon, an unsaturated hydrocarbon, a compound (ketone) including carbonyl, an ester, an ether and an alcohol. Specific examples of the aromatic hydrocarbon include benzene, toluene and xylene. Specific examples of the unsaturated hydrocarbon include limonene and pinene. Specific examples of the ketone include cyclohexanone and methyl ethyl ketone. Specific examples of the ester include butyl acetate. Specific examples of the ether include anisole, 1,4-di(2-hydroxyethoxy)benzene and ethylene glycol monophenyl ether. Specific examples of the alcohol include butanol, pentanol and hexanol. Among these compounds, xylene, toluene, limonene and the like are preferable in that these are easily available, have a refractive index of around 1.5, to thereby allow a mounting agent satisfying the conditions of Expressions (1) and (2) to be easily prepared, and have a drying speed suitable for an operation because of being dried at about several tens minutes.

Examples of the resin compounded to the lipid-soluble mounting agent include synthetic resins such as a styrene resin (polystyrene and the like) and an acrylic resin (polymethyl methacrylate and the like), and natural resins such as canada balsam. These resins are preferable in that these have a refractive index closer to that of glass, and are colorless and transparent, to thereby neither absorb fluorescence of the fluorescent particle nor emit autofluorescence.

In one embodiment of the present invention, the packed layer is preferably a layer formed from a (lipid-soluble) mounting agent containing an acrylic resin, such as products "Entellan new", "PARAmount N" and "Malinol". Such a packed layer has a refractive index n2 which easily satisfies Expressions (1) and (2), when, for example, a fluorescent body-integrated nanoparticle including a resin as a base material is used as the fluorescent particle, and/or cover glass made of borosilicate glass is used as the protection layer.

The mounting agent may also further contain, if necessary, a fading inhibitor (antioxidant, ultraviolet absorber). As the fading inhibitor, for example, at least one selected from the following can be used: phenolic, amine-based, phosphorus, sulfuric and unsaturated hydrocarbon-based fading inhibitors which have no problem in the solubility of the solvent used in the mounting agent. Such a fading inhibitor also preferably emits no light in a wavelength region overlapped with the region of the local maximum emission wavelength (preferably 550 to 650 nm) of the fluorescent particle and also absorbs no light in a wavelength region overlapped with the region of the maximum excitation wavelength of the fluorescent particle so that there is no effect on taking of a fluorescence image.

(Protection Layer)

The protection layer is a layer with which the packed layer is covered, and is typically a layer formed by cover glass.

The protection layer, namely, cover glass forming the protection layer is not particularly limited as long as the refractive index (n3) satisfies the condition of Expression (2), and appropriate one can be selected in consideration of the refractive index (n2) of the packed layer.

In one embodiment of the present invention, the protection layer preferably includes cover glass made of borosilicate glass (soda glass). Such a protection layer has a refractive index n3 easily satisfying Expression (2), when a layer formed from a mounting agent containing an acrylic resin is used as the packed layer, for example. The cover glass made of borosilicate glass generally has a refractive index of 1.51 to 1.53 and a thickness of 0.12 to 0.17 mm.

—Method for Producing Pathological Specimen—

The method for producing a pathological specimen of the present invention includes performing a treatment (immunostaining/FISH staining treatment) for fluorescence-labeling of an objective biomaterial with a fluorescent particle observable in a dark field, based on an immunostaining method or a FISH method; performing a treatment (packing treatment) for covering of the tissue section with a packed layer; and performing a treatment (protection treatment) for covering of the packed layer with a protection layer; wherein the refractive indexes of the fluorescent particle, the packed layer and the protection layer (measurement wavelength=589 nm and measurement temperature=20° C. in all) in the immunostaining/FISH staining treatment, the packing treatment and the protection treatment satisfy the conditions of the following Expressions (1) and (2):

$$|n1-n2| \leq 0.20 \quad \text{Expression (1)}$$

$$|n2-n3| \leq 0.15 \quad \text{Expression (2)}$$

n1: the refractive index of the fluorescent particle
n2: the refractive index of the packed layer
n3: the refractive index of the protection layer.

The method for producing a pathological specimen of the present invention may include various treatments and/or processes included in a common method for producing a pathological specimen, in addition to the immunostaining/FISH staining treatment, the packing treatment and the protection treatment. A common method for producing a pathological specimen includes a specimen pre-treatment, a staining operation and a specimen post-treatment.

In an embodiment where the staining treatment of the objective biomaterial is performed based on the immunostaining method (namely, a protein is used as the objective biomaterial), the specimen pre-treatment includes a deparaffinization treatment, an antigen retrieval treatment, a washing treatment, and the like. The staining operation includes a treatment (immunostaining treatment) for staining based on an immunostaining method, namely, a primary antibody treatment, a secondary antibody treatment, a fluorescent particle treatment or the like depending on whether the objective biomaterial is directly or indirectly labeled, and usually further includes a staining treatment (with, for example, hematoxylin/eosin) for observation of the form. The specimen post-treatment includes a solvent replacement treatment, a packing treatment (a mounting treatment with a mounting agent), a protection treatment, and, if necessary, a washing treatment and a dehydration treatment performed before the solvent replacement treatment.

In an embodiment where the staining treatment of the objective biomaterial is performed based on a FISH method (namely, a nucleic acid having a specified base sequence is used as the objective biomaterial), the specimen pre-treatment includes a deparaffinization treatment, a pre-treatment for FISH, an enzyme (protease) treatment, an immobilization treatment, and the like. The staining operation includes a treatment (FISH staining treatment) for staining based on a FISH method, namely, a DNA modification treatment, a hybridization treatment, a post-hybridization treatment, and the like, and usually further includes a nuclear staining treatment (for example, with DAPI). The specimen post-treatment includes a solvent replacement treatment, a packing treatment (mounting treatment with a mounting agent), a protection treatment, and, if necessary, a washing treatment and a dehydration treatment performed before the solvent replacement treatment.

Hereinafter, treatments and processes required for carrying out the method for producing a pathological specimen of the present invention will be further described. Any matters not particularly described in the present description, with respect to the method for producing a pathological specimen, can be assumed to be encompassed in appropriate embodiments, with reference to, for example, matters described in Patent Documents 1 to 3, or other known or common technical matters thereof.

<Immunostaining/FISH Staining Treatment>

The immunostaining/FISH staining treatment is to label an objective biomaterial with a fluorescent particle (for example, fluorescent body-integrated nanoparticle) based on an immunostaining method or a FISH method. In the immunostaining treatment, a fluorescent particle having a refractive index satisfying the condition of Expression (1) in terms of the relationship with a packed layer (typically mounting agent) for use in a packing treatment described below, preferably a fluorescent body-integrated nanoparticle including a resin as a base material is used. The fluorescent particle to be used is preferably a fluorescent particle (fluorescent body-integrated nanoparticle) where the local maximum emission wavelength ($\lambda 1$) satisfies the condition of Expression (7), namely, 550 nm$\leq \lambda 1 \leq$650 nm. Such a fluorescent particle is as described in the section "pathological specimen".

(Immunostaining Treatment)

There are various immunostaining methods, any immunostaining method can be adopted without any particularly limitation as long as a tissue section can be stained so that an objective protein can be fluorescently labeled and used for a pathological diagnosis and the like, and representative examples include the following:

a method (primary antibody method) including preparing a fluorescently labeled primary antibody where a fluorescent particle and a primary antibody are linked, and directly fluorescence-labeling and staining the fluorescently labeled primary antibody with an objective protein;

a method (secondary antibody method) including preparing a primary antibody, and a fluorescently labeled secondary antibody where a fluorescent particle and a secondary antibody are linked, reacting the primary antibody with an objective protein, and thereafter reacting the fluorescently labeled secondary antibody with the primary antibody, thereby indirectly fluorescence-labeling and staining the objective protein;

a method (primary antibody method with avidin-biotin combination use) including preparing a biotin-modified primary antibody where a primary antibody and biotin are linked, and an avidin-modified fluorescent particle where a fluorescent particle and avidin or streptavidin are linked, reacting the biotin-modified primary antibody with an objective protein, and thereafter further reacting the avidin-modified fluorescent particle therewith, thereby indirectly fluorescence-labeling and staining the objective protein by means of an avidin-biotin reaction; and a method (secondary antibody method with avidin-biotin combination use) including preparing a primary antibody, a biotin-modified secondary antibody where a secondary antibody and biotin are linked, and an avidin-modified fluorescent particle where a fluorescent particle and avidin or streptavidin are linked, reacting the primary antibody with an objective protein, then reacting the biotin-modified secondary antibody therewith, and thereafter further reacting the avidin-modified fluorescent particle therewith, thereby indirectly fluorescence-labeling and staining the objective protein by means of an avidin-biotin reaction.

In the primary antibody method with avidin-biotin combination use or the secondary antibody method with avidin-biotin combination use, hapten (not having immunogenicity, but exhibiting antigenicity, being a substance reactive with an antibody and having a relatively low molecular weight) and an anti-hapten antibody, for example, digoxigein and an anti-digoxigein antibody, FITC (fluorescein isothiocyanate) and an anti-FITC antigen, or furthermore a combination of other substances having the same specific reactivity can also be utilized instead of biotin and avidin.

The immunostaining treatment may be performed according to standard procedures and treatment conditions of each of various methods described above. In general, a tissue section placed on an analyte slide may be brought into contact with at least one reagent according to an embodiment of the immunostaining method (for example, the reagent is dropped on the tissue section, or the tissue section is immersed in the reagent), and reacted at a proper temperature for a proper time (for example, at 4° C. overnight). Various reagents required for immunostaining, namely, solutions such as a buffer solution where a fluorescently labeled primary or secondary antibody, a biotin-modified primary or secondary antibody, an avidin-modified secondary antibody or a fluorescent body, and the like are dissolved, and, if necessary, a blocking agent such as BSA is added thereto, can be produced according to a known method, and can also be available as commercial products.

The objective protein to be immunostained is not particularly limited, and can be typically selected from proteins to be subjected to a pathological diagnosis based on a tissue immunostaining method, such as HER2, TOP2A, HER3, EGFR, P53, MET, and various other proteins derived from cancer/tumor-related genes (so-called biomarker genes), and furthermore cancer-related proteins such as a cancer growth factor, a transcriptional regulator, an amplification regulator receptor and a transcriptional regulator receptor.

The monoclonal antibody and polyclonal antibody (primary antibodies) against the objective protein, and antibodies (secondary antibodies) against such antibodies can be produced according to a known method, and can also be available as commercial products.

(FISH Treatment)

There are various FISH methods, any FISH method can be adopted without any particularly limitation as long as a tissue section can be stained so that an objective gene can be fluorescently labeled and used for a pathological diagnosis and the like, and representative examples thereof include the following:

a method (direct method) including preparing a fluorescently labeled probe where a fluorescent body and a probe are linked, and directly fluorescently labeling and staining an objective gene with the fluorescently labeled probe; and a method (indirect method) including preparing a biotin-modified probe where a probe and biotin are linked, and an avidin-modified fluorescent body where a fluorescent body and avidin or streptavidin are linked, reacting the biotin-modified probe with an objective gene, and thereafter further reacting the avidin-modified fluorescent body therewith, thereby indirectly fluorescently labeling and staining the objective gene by means of an avidin-biotin reaction.

In the above indirect method, hapten (not having immunogenicity, but exhibiting antigenicity, being a substance reactive with an antibody and having a relatively low molecular weight) and an anti-hapten antibody, for example, digoxigein and an anti-digoxigein antibody, FITC (fluorescein isothiocyanate) and an anti-FITC antigen, or furthermore a combination of other substances having the same specific reactivity can also be utilized instead of biotin and avidin.

The FISH method may be performed according to standard procedures and treatment conditions of each of various methods described above. In general, an analyte slide on which a tissue section is placed may be immersed in at least one reagent according to a FISH method, at a proper temperature for a proper time. Various reagents required for FISH, namely, solutions such as a buffer solution where a fluorescently labeled probe, a biotin-modified probe, an avidin-modified fluorescent body, and the like are dissolved, and, if necessary, a blocking agent such as BSA is added thereto, can be produced according to a known method, and can also be available as commercial products. For example, dTTP of a DNA clone of the objective gene can be substituted with biotin-modified dUTP according to a nick translation method, thereby producing a biotin-modified probe to which a plurality of biotins are introduced to a DNA probe.

The objective gene to be subjected to FISH is not particularly limited, and can be typically selected from proteins to be subjected to a pathological diagnosis based on a FISH method, such as HER2, TOP2A, HER3, EGFR, P53, MET, and various other cancer/tumor-related genes (so-called biomarker genes), and furthermore cancer-related proteins such as a cancer growth factor, a transcriptional regulator, an amplification regulator receptor and a transcriptional regulator receptor.

The probe against the objective gene can be produced according to a known method, and can also be available as a commercial product. The base length, the base sequence and the GC content of the probe can be prepared, in consideration of the conditions in hybridization, so that proper stringency is achieved.

<Bright-Field Staining Treatment>

The treatment (bright-field staining treatment) for staining of a cell with a staining agent observable in a bright field may also be performed on the tissue section before or after the immunostaining/FISH staining treatment, or at the same time as the immunostaining treatment.

The bright-field staining treatment can be performed according to standard procedures and treatment conditions. In general, a tissue section placed on an analyte slide may be brought into contact with at least one reagent according to an embodiment of the bright-field staining treatment (for example, the reagent is dropped on the tissue section, or the tissue section is immersed in the reagent), and reacted at a proper temperature for a proper time. The bright-field staining treatment can also be performed at the same time as the immunostaining/FISH staining treatment, as long as the reagent for the bright-field staining treatment is mixed with the reagent for the immunostaining treatment, thereby bringing the mixture into contact with the tissue section placed on an analyte slide.

<Packing Treatment>

The packing treatment (mounting treatment) is a treatment for covering of the tissue section subjected to the immunostaining/FISH staining treatment (and, if necessary, bright-field staining treatment) with the packed layer, and is typically a treatment for mounting of the tissue section with the mounting agent. The packing treatment allows a packed layer to be formed, the packed layer having a refractive index satisfying the condition of Expression (1) in terms of the relationship with the fluorescent particle for use in the immunostaining/FISH staining treatment, and having a refractive index satisfying the condition of Expression (2) in terms of the relationship with a protection layer formed in a protection treatment described below. Typically, a mounting agent having a refractive index satisfying the conditions of Expressions (1) and (2), preferably a mounting agent containing an acrylic resin is used. Such a protection layer (mounting agent) is as described above in the section "pathological specimen".

When a lipid-soluble mounting agent is here used as the mounting agent, it is preferable to perform a treatment (solvent replacement treatment) including removal of an aqueous solvent used in staining, washing and the like and attached to the tissue section, by drying or by use of an alcohol or the like, and replacement with the same type of an organic solvent as that used in the mounting agent, prior to the packing treatment.

The procedure and conditions for the packing treatment are not particularly limited, and, when the mounting agent is used, the mounting agent may be generally dropped on the tissue section on an analyte slide. In addition, the thickness of the packed layer can be constant and also uniform regardless of the amount of the mounting agent dropped, namely, the in-plane variation coefficient can be lower by dropping the mounting agent (the packing treatment), and thereafter, for example, disposing cover glass as the protection layer (in the protection treatment) and then disposing an article serving as a weight on the cover glass and/or pushing the cover glass by tweezers or the like. If such operations are not performed, the thickness of the packed layer varies depending on the amount of the mounting agent dropped, and the thickness of the packed layer usually tends to be thicker as the amount dropped is larger.

The thickness ($m2$) of the packed layer preferably satisfies the condition of Expression (3) in terms of the relationship with the thickness ($m3$) of the protection layer described below, namely: the in-plane variation coefficient (CV ($m2+m3$)) of the sum of $m2$ and $m3$ preferably satisfies CV (m2+m3)≤20%. In addition, the thickness (m2) of the packed layer preferably satisfies the condition of Expression (4), namely, the in-plane average (M (m2)) of m2 preferably satisfies 10 m≤M (m2)≤50 μm. A packed layer having such a preferable thickness can be formed by regulating the amount of the mounting agent dropped, and/or applying force to the cover glass, as described above.

<Protection Treatment>

The protection treatment is a treatment for covering of the tissue section subjected to the packing treatment (mounting treatment), with the protection layer, and is typically a treatment for placement of cover glass. The protection treatment allows a protection layer to be formed, the protection layer having a refractive index satisfying the condition of Expression (2) in terms of the relationship with the packed layer formed in the packing treatment. Typically, cover glass having a refractive index satisfying the condition of Expression (2), preferably cover glass made of borosilicate glass is used. Such a protection layer (cover glass) is as described above in the section "pathological specimen".

The procedure and conditions for the protection treatment are not particularly limited, and, when the cover glass is used, the cover glass may be generally placed on the packed layer formed so that the tissue section is covered. The thickness of the cover glass used corresponds to the thickness of the protection layer. The thickness of the packed layer can be constant and also uniform, namely, the in-plane variation coefficient can be lower by disposing an article serving as a weight on the cover glass and/or pushing the cover glass by tweezers or the like, as described above, in placement of the cover glass.

The thickness (m3) of the protection layer preferably satisfies the condition of Expression (3) in terms of the relationship with the thickness (m2) of the packed layer, namely, the in-plane variation coefficient (CV (m2+m3)) of the sum of m2 and m3 preferably satisfies CV (m2+m3) ≤20%. In addition, the thickness (m3) of the protection layer preferably satisfies the condition of Expression (5), namely, the in-plane average (M (m3)) of m3 preferably satisfies 100 μm≤M (m3)≤200 μm. A protection layer having such a preferable thickness can be formed by selecting and using proper cover glass.

—Method for Acquiring Fluorescence Image—

The method for acquiring a fluorescence image of the present invention is a method for acquiring a fluorescence image of the pathological specimen of the present invention, or a pathological specimen obtained by the production method of the present invention, including: measuring the thickness (m2) of the packed layer and the thickness (m3) of the protection layer in the pathological specimen, thereby calculating the in-plane average (M (m2+m3)) of the sum of m2 and m3; and correcting the spherical aberration of a bright spot image of the fluorescent particle based on the in-plane average.

Hereinafter, the system and apparatus for carrying out the method for acquiring a fluorescence image of the present invention will be more specifically described with reference to one embodiment where not only a fluorescence image, but also a bright field image is acquired. Any matters not particularly described in the present specification, with respect to the respective methods for acquiring a fluorescence image and a bright field image, or the image processing method and analysis method of the fluorescence image and the bright field image acquired, can be assumed to be encompassed in appropriate embodiments, with reference to, for example, matters described in Patent Documents 1 to 3, or other known or common technical matters thereof.

In the present embodiment, the fluorescence image and the bright field image are taken by a microscopic image-acquiring apparatus having a structure according to a known camera-equipped fluorescence microscope. The microscopic image-acquiring apparatus is connected to an image processing apparatus so as to be able to transmit/receive data thereto/therefrom via an interface such as a cable, and thus forms a pathological diagnosis support system. Thus, image data acquired with respect to a tissue section on a slide (pathological specimen) placed on a slide fixed stage can be rapidly transmitted to the image processing apparatus, and thus utilized in image processing and analysis for a pathological diagnosis.

The field of the microscope image preferably has an area of 3 $mm^2$ or more, more preferably 30 $mm^2$ or more, further preferably 300 $mm^2$ or more. The field of the microscope image corresponds to the fluorescence image and the bright field image taken.

The microscopic image-acquiring apparatus includes an irradiation device, a focusing device, an imaging device, a thickness measurement device, a communication I/F, and the like. The irradiation device includes a light source, a filter and the like, and irradiates the tissue section on a slide placed on a slide fixed stage with light. The focusing device includes an eye lens, an objective lens, a spherical aberration correction mechanism, and the like, and focuses transmitted light, reflected light or fluorescence released from the tissue section on a slide due to irradiation light. The imaging device includes a CCD (Charge Coupled Device) sensor and the like, and corresponds to a camera disposed on a microscope, the camera taking an image formed on a focusing surface by the focusing device to thereby produce the digital image data of a microscope image. The communication I/F transmits the image data produced of a microscope image, to the image processing apparatus.

The microscopic image-acquiring apparatus includes a bright field unit where an irradiation device and a focusing device suitable for bright field observation are combined, and a fluorescence unit where an irradiation device and a focusing device suitable for fluorescence observation are combined, and such units can be switched, thereby switching acquiring of a bright field image or a fluorescence image as a microscope image. An excitation light source and an optical filter for fluorescence detection, of the fluorescence unit, are selected depending on the local maximum excitation wavelength and the local maximum emission wavelength of the fluorescent particle used in immunostaining.

On the other hand, the image processing apparatus includes a controller, an operating portion, a display, a communication I/F, a memory, and the like, and these are connected via buses. The controller includes CPU (Central Processing Unit), RAM (Random Access Memory), and the like, and executes various processing in cooperation with various programs stored in the memory, thereby generally controlling actions of the image processing apparatus. For example, the controller executes image analysis processing in cooperation with programs stored in the memory. The operating portion includes a keyboard including character input keys, number input keys and various function keys, as well as a pointing device such as a mouse, and outputs a depression signal from a key depressed by the keyboard and a manipulated signal from the mouse as input signals to the controller. The display includes, for example, a monitor such as LCD (Liquid Crystal Display), and functions as an output device for displaying various screens according to the instruction of the display signal input from the controller, namely, for outputting the image analysis result. The communication I/F is an interface for transmitting or receiving data to or from external instruments including a microscopic image-acquiring apparatus. The communication I/F functions as an input device of a bright field image and a fluorescence image. The memory includes, for example, HDD (Hard Disk Drive) and a semiconductor non-volatile memory. The memory stores various programs, various data, and the like as described above. Additionally, the image processing apparatus includes a LAN adaptor, a router and the like, and may also be formed so as to be connected to an external instrument via a communication network such as LAN.

The bright field image and the fluorescence image are acquired according to the following Procedures (1) to (5).
(1) Place the pathological specimen (analyte slide) subjected to the bright-field staining treatment and the immunostaining/FISH staining treatment, onto the slide fixed stage of the microscopic image-acquiring apparatus.
(2) Select the bright field unit, perform photographing magnification and focus adjustments, and put the area to be observed of the tissue section, into the field.
(3) Perform photographing by the imaging device, thereby producing image data of the bright field image, and transmit the image data to the image processing apparatus.
(4) Change the unit to the fluorescence unit.
(5) Perform photographing by the imaging device without any changes in field and photographing magnification, thereby producing image data of the fluorescence image, and transmit the image data to the image processing apparatus.

In a preferable embodiment of the present invention, the followings are performed before photographing by the imaging device in Procedure (5): measurement of the thickness (m2) of the packed layer and the thickness (m3) of the protection layer in the pathological specimen by the thickness measurement device, and thus calculation of the in-plane average (M (m2+m3)) of the sum of m2 and m3; and correction of the spherical aberration of a bright spot image of the fluorescent particle by the spherical aberration correction mechanism, based on the in-plane average.

The thickness measurement device with which the microscopic image-acquiring apparatus is provided can be constructed with reference to any device with which a thickness measurement apparatus in the form of a known microscope such as a confocal laser scanning microscope or a microscope (digital microscope) is provided. The respective thicknesses m1, m2 and m3 can be separately measured even at a position where the tissue section, the packed layer and the protection layer are stacked. The thicknesses m1, m2 and m3 can be measured at a plurality of points on one field (in-plane), thereby allowing the in-plane averages M (m1), M (m2) and M (m3), and M (m2+m3), as well as the in-plane variation coefficient CV (m2+m3) to be calculated. When m1, m2 and m3 are not required to be separately measured, for example, the sum (m2+m3) of the thicknesses of the packed layer and the protection layer may be measured in order to discriminate whether Expression (3) is satisfied or not, an embodiment can also be adopted where the thicknesses of two layers: the packed layer and the protection layer; are collectively measured.

The measurement data of each of m1, m2 and m3 may be transmitted to the image processing apparatus and stored in the memory included in the image processing apparatus for computation on the controller, or may be stored in the memory for computation on the controller in the case where the microscopic image-acquiring apparatus includes the same memory and controller.

When one or more of Expression (3) to (6) is/are found not to be satisfied as a result of measurement of m1, m2 and m3 on a certain field (in-plane), the field may be changed to another field and m1, m2 and m3 in the another field may be measured, thereby allowing the fluorescence image to be acquired in the case of a desired expression being satisfied.

The spherical aberration correction mechanism with which the microscopic image-acquiring apparatus is provided can be constructed with reference to any device with which a known fluorescence microscope or other microscope (scanning transmission electron microscope or the like) is provided. The spherical aberration correction mechanism reads the CV (m2+m3) value calculated from the thickness data obtained by measurement with the thickness measurement device, thereby allowing the effect of spherical aberration correction to be automatically optimized based on the value. For example, the spherical aberration correction mechanism includes a concave lens for aberration correction, and can be constructed so that the concave lens for aberration correction can be disposed at a position where the effect of spherical aberration correction is optimized.

Examples

[1-1] Production of Fluorescent Body-Integrated Nanoparticle (Sulforhodamine-Integrated Melamine Resin Particle)

In 22 mL of water was dissolved 14.4 mg of SulfoRhodamine 101 (produced by Sigma-Aldrich) (excitation wavelength: 586 nm, emission wavelength: 605 nm) being a red light emitting dye, as a fluorescent dye. Thereafter, 2 mL of a 5% aqueous solution of "Emulsion (registered trademark) 430" (polyoxyethylene oleyl ether, produced by Kao Corporation) being an emulsifier for emulsion polymerization was added to the solution. After the solution was heated to 70° C. with stirring on a hot stirrer, 0.65 g of "Nikalac MX-035" (produced by NIPPON CARBIDE INDUSTRIES CO., INC.) being a melamine resin raw material was added to the solution. Furthermore, 1000 µL of a 10% aqueous solution of dodecylbenzenesulfonic acid (produced by KANTO KAGAKU) being a surfactant was added to the solution, and heated and stirred at 70° C. for 50 minutes. Thereafter, the resultant was heated to 90° C. and stirred for 20 minutes with heating. Washing with pure water was performed in order to remove impurities such as excess resin raw material and fluorescent dye from the resulting dispersion liquid of the dye resin particle. Specifically, centrifugation was made by a centrifuge machine "Micro Cooling Centrifuge 3740" (manufactured by KUBOTA CORPORATION) at 20000 G for 15 minutes, the supernatant was removed, thereafter ultrapure water was added, and ultrasonic irradiation was made for re-dispersion. Washing including centrifugation, removal of the supernatant, and re-dispersion into ultrapure water was repeated five times. Finally, the fluorescent body-integrated nanoparticle prepared as above was recovered by centrifugation, and stored in the state of being dispersed in PBS. The resulting sulforhodamine-integrated melamine resin particle was observed with SEM, and was found to have an average particle size of 115 nm and a variation coefficient of 13%.

[1-2] Production of Fluorescent Body-Integrated Nanoparticle (Tetramethylrhodamine-Integrated Silica Particle)

Tetramethylrhodamine (6.6 mg) (produced by Invitrogen, TAMRA-SE) (excitation wavelength: 550 nm, emission wavelength: 570 nm) and 3 µL of 3-aminopropyltrimethoxysilane (produced by Shin-Etsu Chemical Co., Ltd., KBM903) were mixed in DMF, thereby providing an organoalkoxysilane compound. The resulting organoalkoxysilane compound (0.6 ml) was mixed with 48 ml of ethanol, 0.6 ml of TEOS (tetraethoxysilane), 2 ml of water and 2 ml of 28% ammonia water for 3 hours. The mixed liquid prepared in the above operation was subjected to centrifugation at 10000 G for 20 minutes, and the supernatant was removed. Ethanol was added thereto, thereby dispersing a precipitate, and the resultant was again subjected to centrifugation. Washing with each of ethanol and pure water was performed by the same procedure twice. The resulting tetramethylrhodamine-integrated silica nanoparticle was observed with SEM, and was found to have an average particle size of 104 nm and a variation coefficient of 12%.

[2-1] Production of Model Preparation

[Preparation A1]

(1) A PBS dispersion liquid including the fluorescent body-integrated nanoparticle (sulforhodamine-integrated melamine resin particle refractive index (n1)=1.48) produced in [1-1], in a concentration of 0.01 nM, was prepared. On APS (aminosilane)-coated glass (Matsunami Glass Ind., Ltd.) was placed 80 µL of the PBS dispersion liquid, and left to stand for 60 minutes.

(2) The slide in (1) was washed with PBS (5 minutes×3 times). A reagent for hematoxylin staining was placed and left to stand for 10 minutes. The slide was washed with water (10 minutes), and thereafter sequentially treated with ethanol, dehydrated ethanol three times, and xylene twice.

(3) PIPETMAN was used to drop 25 µL of a mounting agent "Entellan (registered trademark) new refractive index (n2)=1.49" (Merck KGaA).

(4) Cover glass made of borosilicate glass (24 mm×24 mm) (refractive index (n3)=1.51) was gently placed on the mounting agent dropped in (3), and thereafter strongly pressed by tweezers.

(5) The resultant was left to stand until the mounting agent was dried, thereby completing preparation A1. Additional two of preparations A1, three in total, were produced by the same procedure.

Values n1 to n3 satisfied the following Expression (1) and Expression (2).

$$|n1-n2| \leq 0.20 \quad \text{Expression (1)}$$

$$|n2-n3| \leq 0.15 \quad \text{Expression (2)}$$

[Preparation A2]

Three preparations A2 in total were produced by the same procedure as in preparation A1 except that the amount of the mounting agent dropped in (3) was changed to 50 µL.

[Preparation A3]

Three preparations A3 in total were produced by the same procedure as in preparation A1 except that the amount of the mounting agent dropped in (3) was changed to 75 µL.

[Preparation A4]

Three preparations A4 in total were produced by the same procedure as in preparation A1 except that the amount of the mounting agent dropped in (3) was changed to 100 µL.

[Preparation A5]

Three preparations A5 in total were produced by the same procedure as in preparation A1 except that the amount of the mounting agent dropped in (3) was changed to 150 µL.

[Preparation A6]

Three preparations A6 in total were produced by the same procedure as in preparation A1 except that the amount of the mounting agent dropped in (3) was changed to 200 µL.

[Preparation B1]

Three preparations B1 in total were produced by the same procedure as in preparation A1 except that the cover glass was merely gently placed on the mounting agent in (4) and was not pressed by tweezers.

[Preparation B2]

Three preparations B2 in total were produced by the same procedure as in preparation A1 except that the cover glass was merely gently placed on the mounting agent in (4) and was not pressed by tweezers and the amount of the mounting agent dropped in (3) was changed to 50 µL.

[Preparation B3]

Three preparations B3 in total were produced by the same procedure as in preparation A1 except that the cover glass was merely gently placed on the mounting agent in (4) and was not pressed by tweezers and the amount of the mounting agent dropped in (3) was changed to 75 µL.

[Preparation B4]

Three preparations B4 in total were produced by the same procedure as in preparation A1 except that the cover glass was merely gently placed on the mounting agent in (4) and was not pressed by tweezers and the amount of the mounting agent dropped in (3) was changed to 100 µL.

[Preparation B5]

Three preparations B5 in total were produced by the same procedure as in preparation A1 except that the cover glass was merely gently placed on the mounting agent in (4) and was not pressed by tweezers and the amount of the mounting agent dropped in (3) was changed to 150 µL.

[Preparation B6]

Three preparations B6 in total were produced by the same procedure as in preparation A1 except that the cover glass was merely gently placed on the mounting agent in (4) and was not pressed by tweezers and the amount of the mounting agent dropped in (3) was changed to 200 µL.

[3-1] Measurements of Thickness of Packed Layer, Thickness of Protection Layer, and Fluorescence Brightness The three of each of preparations A1 to A6 and B1 to B6, produced as described above, were subjected to measurements of the thickness of the packed layer (the layer formed from the mounting agent), the thickness of the protection layer, and the fluorescence brightness by the following procedures.

[3-1-1] Measurements of Thickness of Packed Layer (Layer Formed from Mounting Agent) and Thickness of Protection Layer The thickness of the packed layer and the thickness of the protection layer of each sample produced were measured with a laser displacement meter "LT-9000" (manufactured by KEYENCE CORPORATION). The measurement was made with respect to seventeen points in total, including the center of the cover glass, four points on each of the diagonal lines of the cover glass, and four points on each of the vertical and horizontal lines passing through the center of the cover glass. The average of the sum of the thickness of the packed layer and the thickness of the protection layer at such seventeen points was defined as the in-plane average (the ordinate axis of the graph in the left portion of FIG. 2) of the sum (m2+m3) of the thickness of the packed layer and the thickness of the protection layer of each sample (preparation).

[3-1-2] Measurement of Fluorescence Brightness

The brightness of each sample produced was measured with a fluorescence microscope. An upright microscope "Axio Imager M2" (manufactured by Carl Zeiss) was used to acquire a fluorescent spot image with the objective lens being set to a magnification of 40×. When a fluorescence image was acquired, the fluorescent body-integrated nanoparticle made of the sulforhodamine-integrated melamine resin particle was irradiated with excitation light having a wavelength of 580 nm and an intensity of 30 mW, thereby focusing fluorescence having a wavelength of 605 nm emitted from the fluorescent body-integrated nanoparticle, to acquire a microscope image (image data) by a camera (monochrome) installed in the microscope. The camera here had a pixel size of 6.4 μm×6.4 m, a number of vertical pixels of 1040, and a number of horizontal pixels of 1388 (imaging area: 8.9 mm×6.7 mm). The measurement points were the same seventeen points as the positions in the measurements of the thickness of the layer from the mounting agent and the thickness of the protection layer described above. The resulting data was analyzed as follows: the fluorescence intensity was calculated based on the fluorescence image obtained at each measurement point, and the average thereof at the seventeen points was obtained and thus defined as the in-plane average (the ordinate axis of the graph in the right portion of FIG. 2) of the fluorescence brightness of each sample (preparation). The fluorescence intensity obtained at each measurement point was obtained by reading the brightness signal value at the fluorescent spot of individual fluorescent body-integrated nanoparticle scattered in the image taken and averaging the resultant.

[3-1-3] Results

The results are illustrated in FIG. 2. It was found with respect to preparations A1 to A6 where any weight was applied to the cover glass that the layer formed from the mounting agent was almost uniform in thickness regardless of the amount of the mounting agent added and the difference among the samples produced in the same conditions (the upper left of FIG. 2) and thus was also almost uniform in fluorescence brightness (the upper right of FIG. 2). On the other hand, it was found with respect to preparations B1 to B6 where no weight was applied to the cover glass that an increase in the amount of the mounting agent tended to cause an increase in the thickness and uniform thickness was not obtained (the lower left of FIG. 2), the fluorescence brightness was also plotted with a chevron curve being drawn, and thus was not uniform and was relatively largely varied even among the samples produced in the same conditions (the lower right of FIG. 2).

[2-2] Production of Model Preparation

[Preparation A7]

One preparation A7 was produced by the same procedure as in preparation A1 except that the amount of the mounting agent dropped in (3) of [2-1] was changed to 100 μL.

[Preparation A8]

One preparation A8 was produced by the same procedure as in preparation A1 except that the fluorescent body-integrated nanoparticle (tetramethylrhodamine-integrated silica particle) produced in [1-2] was used in (1) of [2-1] and the amount of the mounting agent dropped in (3) of [2-1] was changed to 100 μL.

[Preparation B7]

One preparation B7 was produced by the same procedure as in preparation A1 except that a quantum dot "CdSe/ZnS 610" (produced by Sigma-Aldrich, particle size: 5.2 nm) was used in (1) of [2-1] and the amount of the mounting agent dropped in (3) of [2-1] was changed to 100 μL.

[Preparation B8]

One preparation B8 was produced by the same procedure as in preparation A1 except that the fluorescent body-integrated nanoparticle (tetramethylrhodamine-integrated silica particle) produced in [1-2] was used in (3) of [2-1], an ultraviolet curable fluorine-containing resin "Defenser OP-3801" (produced by DIC CORPORATION, uncured) was used as the mounting agent, and the amount of the mounting agent dropped in (3) of [2-1] was changed to 100 μL.

[Preparation B9]

One preparation B9 was produced by the same procedure as in preparation A1 except that the fluorescent body-integrated nanoparticle (tetramethylrhodamine-integrated silica particle) produced in [1-2] was used in (3) of [2-1], a-bromonaphthalene-2-methyl acrylate (uncured) was used as the mounting agent, and the amount of the mounting agent dropped in (3) of [2-1] was changed to 100 μL.

[3-2] Measurement of in-Plane Fluorescence Brightness

Each of preparations A7 to A8 and B7 to B9 was subjected to brightness measurement, and the in-plane brightness variation coefficient was calculated.

[3-2-1] Measurement of Fluorescence Brightness

The fluorescence brightness was measured at in-plane seventeen points by the same procedure as in [3-1-2], and the variation coefficient was calculated. The measurement using the fluorescent body-integrated nanoparticle made of the tetramethylrhodamine-integrated silica particle (each of preparations A8, B8 and B9) was performed so that irradiation with excitation light having a wavelength of 550 nm and an intensity of 30 mW was made and fluorescence having a wavelength of 570 nm emitted from the fluorescent body-integrated nanoparticle was focused. The measurement using the quantum dot (preparation B7) was performed so that irradiation with excitation light having a wavelength of 490 nm and an intensity of 30 mW was made and fluorescence having a wavelength of 610 nm emitted from the quantum dot was focused.

[3-2-2] Results

The results are indicated in Table 1. It was found with respect to preparations A7 and A8 where the difference in refractive index satisfied both of Expressions (1) and (2) that the in-plane variation coefficient of the fluorescence brightness was relatively low and the variation was suppressed. On the other hand, it was found with respect to preparations B7 to B9 where the difference in refractive index did not satisfy Expression (1) or (2) that the in-plane variation coefficient of the fluorescence brightness was relatively high and the variation was easily caused even in the same plane.

TABLE 1

| | Refractive index | | | Difference in refractive index | | In-plane variation |
|---|---|---|---|---|---|---|
| | Fluorescent particle | Packed layer | Protection layer | $\|n1 - n2\| \leq 0.20 \ldots$ Expression (1) | | coefficient of fluorescence |
| Preparations | n1 | n2 | n3 | $\|n1 - n2\|$ | $\|n2 - n3\|$ | brightness |
| A7 | Melamine resin particle 1.48 | Entellan new 1.49 | Cover glass 1.51 | 0.01 | 0.02 | 13% |

TABLE 1-continued

| | Refractive index | | | Difference in refractive index | | In-plane variation |
|---|---|---|---|---|---|---|
| | Fluorescent particle | Packed layer | Protection layer | $\|n1 - n2\| \leq 0.20 \ldots$ Expression (1) | | coefficient of fluorescence |
| Preparations | n1 | n2 | n3 | $\|n1 - n2\|$ | $\|n2 - n3\|$ | brightness |
| A8 | Silica particle 1.49 | Entellan new 1.49 | Cover glass 1.51 | 0.00 | 0.02 | 15% |
| B7 | Quantum dot 3.8 | Entellan new 1.49 | Cover glass 1.51 | 2.31 | 0.02 | 23% |
| B8 | Silica particle 1.49 | Defenser OP 1.35 | Cover glass 1.51 | 0.14 | 0.16 | 25% |
| B9 | Silica particle 1.49 | Entellan new 1.49 | α-Bromo-naphthalene-2-methyl acrylate 1.66 | 0.00 | 0.17 | 21% |

[2-3] Production of Model Preparation

[Preparation A9]

One preparation A9 was produced by the same procedure as in preparation A1 except that the amount of the mounting agent dropped in (3) of [2-1] was changed to 100 μL.

[Preparation A10]

One preparation A10 was produced by the same procedure as in preparation A1 except that the amount of the mounting agent dropped in (3) of [2-1] was changed to 300 μL.

[Preparation A11]

One preparation A11 was produced by the same procedure as in preparation A1 except that the amount of the mounting agent dropped in (3) of [2-1] was changed to 10 μL.

[Preparation A12]

One preparation A12 was produced by the same procedure as in preparation A1 except that the amount of the mounting agent dropped in (3) of [2-1] was changed to 800 μL.

[3-3] Measurement of in-Plane Fluorescence Brightness

Each of preparation A9 to A12 was subjected to measurements of the thickness of the packed layer (the layer formed from the mounting agent) and the fluorescence brightness by the following procedure, and the in-plane variation coefficient of the sum of the thickness of the packed layer and the thickness of the protection layer, and the in-plane brightness variation coefficient were calculated. The thickness of the protection layer was here assumed to be 150 μm being a defined value of a cover glass product.

[3-3-1] Measurement of Thickness of Packed Layer

The thickness of the packed layer was measured at the in-plane seventeen points by the same procedure as in [3-1-1]. On the other hand, 150 μm being a defined value as described above was assumed to be the measurement value and the in-plane average at each point, with respect to the thickness of the protection layer. Furthermore, the in-plane variation coefficient of the sum of the thickness of the packed layer and the thickness of the protection layer was calculated from the above value.

[3-3-2] Measurement of Fluorescence Brightness

The fluorescence brightness was measured at in-plane seventeen points by the same procedure as in [3-1-2], and the variation coefficient was calculated.

[3-3-3] Results

The results are indicated in Table 2. It was found with respect to preparations A9 and A10 where the thicknesses of the packed layer and the protection layer satisfied the conditions of Expressions (4) and (5) that the in-plane variation coefficient of the fluorescence brightness was relatively low and the variation was suppressed. On the other hand, while the in-plane variation coefficient of the fluorescence brightness with respect to preparations A11 and A12 where the thicknesses of the packed layer and the protection layer did not satisfy Expression (4) or (5) was relatively low, it was slightly higher than that with respect to preparations A9 and A10.

TABLE 2

| | Thickness | | | |
|---|---|---|---|---|
| Preparations | In-plane average of packed layer M (m2)[μm] 10 μm ≤ M (m2) ≤ 50 μm Expression (4) | In-plane average of protection layer M (m3)[μm] 100 μm ≤ M (m3) ≤ 200 μm Expression (5) | In-plane variation coefficient CV (m2 + n3) CV (m2 + m3) ≤ 20% Expression (3) | In-plane variation coefficient of fluorescence brightness |
| A9 | 20 | 150 | 7% | 13% |
| A10 | 30 | 150 | 8% | 15% |
| A11 | 4 | 150 | 14% | 18% |
| A12 | 70 | 150 | 15% | 19% |

The above experiments were performed in a simulated manner and were not performed with any tissue section subjected to fluorescence staining. It, however, is clear from the above results that the advantageous effects of the present invention are exerted, namely, a fluorescence signal can be stably acquired at a high sensitivity even when the objective biomaterial on the tissue section is actually fluorescently labeled by immunostaining with the fluorescent body-integrated nanoparticle.

REFERENCE SIGNS LIST

1: pathological specimen
2: slide glass
3: tissue section (thickness: m1)
4: fluorescent particle (refractive index: n1)
5: packed layer (refractive index: n2, thickness: m2)
6: protection layer (refractive index: n3, thickness: m3)

The invention claimed is:

1. A pathological specimen comprising: a tissue section for fluorescence-labeling of an objective substance, the tissue section comprising a fluorescent particle observable in a dark field, based on an immunostaining method or a FISH method; a packed layer with which the tissue section is covered; and a protection layer with which the packed layer is covered; wherein
the fluorescent particle is a fluorescent body-integrated particle comprising a plurality of fluorescent bodies encapsulated or attached into a base material, or onto a surface of the base material;
the refractive indexes of the fluorescent particle, the packed layer and the protection layer (measurement wavelength=589 nm and measurement temperature=20° C. in all) satisfy the conditions of the following Expressions (1) and (2):

$|n1-n2| \leq 0.20$  Expression (1)

$|n2-n3| \leq 0.15$  Expression (2)

n1: the refractive index of the fluorescent particle
n2: the refractive index of the packed layer
n3: the refractive index of the protection layer; and
the thicknesses of the packed layer and the protection layer satisfy the condition of the following Expression (3):

$CV(m2+m3) \leq 20\%$  Expression (3)

m2: the thickness of the packed layer
m3: the thickness of the protection layer
CV (m2+m3): the in-plane variation coefficient of the sum of m2 and m3.

2. The pathological specimen according to claim 1, wherein the thicknesses of the packed layer and the protection layer satisfy the conditions of the following Expressions (4) and (5):

$10 \text{ μm} \leq M(m2) \leq 50 \text{ μm}$  Expression (4)

$100 \text{ μm} \leq M(m3) \leq 200 \text{ μm}$  Expression (5)

m2: the thickness of the packed layer
m3: the thickness of the protection layer
M (m2): the in-plane average of m2
M (m3): the in-plane average of m3.

3. The pathological specimen according to claim 1, wherein the fluorescent particle is a fluorescent body-integrated nanoparticle including a resin as a base material.

4. The pathological specimen according to claim 1, wherein the packed layer is a layer formed from a mounting agent containing an acrylic resin.

5. The pathological specimen according to claim 1, wherein the protection layer is cover glass made of borosilicate glass.

6. The pathological specimen according to claim 1, wherein the thickness of the tissue section satisfies the condition of the following Expression (6):

$2 \text{ μm} \leq M(m1) \leq 6 \text{ μm}$  Expression (6)

m1: the thickness of the tissue section
M (m1): the in-plane average of m1.

7. The pathological specimen according to claim 1, wherein the emission wavelength of the fluorescent particle satisfies the condition of the following Expression (7):

$550 \text{ nm} \leq \lambda1 \leq 650 \text{ nm}$  Expression (7)

λ1: the local maximum emission wavelength of the fluorescent particle.

8. The pathological specimen according to claim 1, wherein the tissue section contains a stained cell that is observable in a bright field.

9. A method for acquiring a fluorescence image of the pathological B specimen according to claim 1, comprising:
measuring the thickness (m2) of the packed layer and the thickness (m3) of the protection layer in the pathological specimen, thereby calculating the in-plane average (M (m2+m3)) of the sum of m2 and m3; and
correcting the spherical aberration of a bright spot image of the fluorescent particle based on the in-plane average.

10. A method for producing a pathological specimen of claim 1, comprising: performing a treatment (immunostaining/FISH staining treatment) for fluorescence-labeling of an objective substance with a fluorescent particle observable in a dark field, based on an immunostaining method or a FISH method; performing a treatment (packing treatment) for covering of the tissue section with a packed layer, and performing a treatment (protection treatment) for covering of the packed layer with a protection layer; wherein
the refractive indexes of the fluorescent particle, the packed layer and the protection layer (measurement wavelength=589 nm and measurement temperature=20° C. in all) in the immunostaining/FISH staining treatment, the packing treatment and the protection treatment satisfy the conditions of the following Expressions (1) and (2):

$|n1-n2| \leq 0.20$  Expression (1)

$|n2-n3| \leq 0.15$  Expression (2)

n1: the refractive index of the fluorescent particle
n2: the refractive index of the packed layer
n3: the refractive index of the protection layers; and the thicknesses of the packed layer and the protection layer satisfy the condition of the following Expression (3) are formed in the packing treatment and the protection treatment:

$CV(m2+m3) < 20\%$  Expression (3)

m2: the thickness of the packed layer
m3: the thickness of the protection layer
CV (m2+m3): the in-plane variation coefficient of the sum of m2 and m3.

11. The method for producing a pathological specimen according to claim 10, wherein a packed layer and a protection layer whose thicknesses satisfy the conditions of the following Expressions (4) and (5) are formed in the packing treatment and the protection treatment:

$10 \text{ μm} \leq M(m2) \leq 50 \text{ μm}$  Expression (4)

$100 \text{ μm} \leq M(m3) \leq 200 \text{ μm}$  Expression (5)

m2: the thickness of the packed layer
m3: the thickness of the protection layer
M (m2): the in-plane average of m2
M (m3): the in-plane average of m3.

12. The method for producing a pathological specimen according to claim 10, wherein a fluorescent body-integrated nanoparticle including a resin as a base material is used as the fluorescent particle in the immunostaining/FISH staining treatment.

13. The method for producing a pathological specimen according to claim 10, wherein the packed layer is formed using a mounting agent containing an acrylic resin in the packing treatment.

14. The method for producing a pathological specimen according to claim 10, wherein the protection layer is formed using cover glass made of borosilicate glass in the protection treatment.

15. The method for producing a pathological specimen according to claim 10, wherein a tissue section whose thickness satisfies the condition of the following Expression (6) is used in the immunostaining/FISH staining treatment:

$$2 \text{ μm} \leq M(m1) \leq 6 \text{ μm} \qquad \text{Expression (6)}$$

m1: the thickness of the tissue section
M (m1): the in-plane average of m1.

16. The method for producing a pathological specimen according to claim 10, wherein a fluorescent particle whose emission wavelength satisfies the condition of the following Expression (7) is used in the immunostaining/FISH staining treatment:

$$550 \text{ nm} \leq \lambda 1 \leq 650 \text{ nm} \qquad \text{Expression (7)}$$

$\lambda 1$: the local maximum emission wavelength of the fluorescent particle.

17. The method for producing a pathological specimen according to claim 10, wherein the tissue section is subjected to a treatment (bright-field staining treatment) for staining of a cell with a staining agent observable in a bright field, before or after the immunostaining/FISH staining treatment, or at the same time as the immunostaining/FISH staining treatment.

* * * * *